US00PP23091P3

(12) United States Plant Patent
Kordes

(10) Patent No.: US PP23,091 P3
(45) Date of Patent: Oct. 2, 2012

(54) FLORIBUNDA ROSE PLANT NAMED 'KORCASTRAV'

(50) Latin Name: *Rosa hybrida*
Varietal Denomination: KORcastrav

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,248

(22) Filed: Oct. 14, 2010

(65) Prior Publication Data

US 2011/0035851 P1 Feb. 10, 2011

(51) Int. Cl.
*A01H 5/00* (2006.01)

(52) U.S. Cl. ..... Plt./150

(58) Field of Classification Search ..... Plt./151, Plt./150, 149, 139
See application file for complete search history.

(56) References Cited

U.S. PATENT DOCUMENTS

PP20,732 P2 * 2/2010 Kordes ..... Plt./108

* cited by examiner

*Primary Examiner* — June Hwu

(57) ABSTRACT

A new and distinct variety of rose with long lasting, novel deep red flowers, and attractive foliage with good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORcastrav'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2000. The crossing was between an unnamed seedling and another unnamed seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORcastrav'.

SUMMARY OF THE INVENTION

The new rose plant may be distinguished from its seed parent, an unnamed seedling, by the following combination of characteristics:

1. The common flower color of 'KORcastrav' is deep red. The common flower color of the unnamed seedling is red-orange.

2. The growth habit of 'KORcastrav' is erect. The unnamed seedling has an arching growth habit.

The new rose plant may be distinguished from its pollen parent, an unnamed seedling, by the following combination of characteristics:

1. The average height of 'KORcastrav' is 60 cm. The average height of the unnamed seedling is 120 cm.
2. 'KORcastrav' blooms in rich clusters of 5-7. The unnamed seedling blooms singly.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORcastrav' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORcastrav' was selected in May, 2001 from the seedling beds to be asexually propagated for further evaluation. The first asexual propagation of 'KORcastrav' was done by budding to seedling understocks in July, 2001 at the inventor's nursery in Offenseth-Sparrieshoop, Germany.

This initial and other subsequent propagations conducted in controlled environments demonstrate that 'KORcastrav' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORcastrav'.

DETAILED BOTANICAL DESCRIPTION

The following is a description of 'KORcastrav', as observed growing in October, 2010 in a nursery in Jackson County, Oreg. on plants of 5 years of age. Color references are made using The Royal Horticultural Society (London, England) Colour Chart, 2001 except where common terms of color are used.

For a comparison, several physical characteristics of the rose variety 'KORsineo', a rose variety from the same inventor described and illustrated in U.S. Plant Pat. No. 20,743 and issued on Feb. 9, 2010 are compared to 'KORcastrav' in Chart 1.

CHART 1

| Characteristic | 'KORcastrav' | 'KORsineo' |
|---|---|---|
| Common flower color | Deep Red | Violet Red |
| Diameter of Plant | 60 cm | 30 cm |
| Flower diameter | 60 mm | 35 mm |

Parents:

*Seed parent.*—An unnamed seedling.

*Pollen parent.*—An unnamed seedling.

Classification:

*Botanical classification.*—*Rosa hybrida,* 'KORcastrav'.

*Commercial classification.*—Floribunda rose.

FLOWER AND FLOWER BUD

Blooming habit: Recurrent.

Flower bud:

*Size.*—Upon opening, 35 mm in length from base of receptacle to end of bud and 25 mm diameter at its widest point.

*Bud form.*—Long. High centered.

*Bud color.*—As sepals first unfold, bud color is Red Group 45B. When ¼ open, the upper surface of petals is Red Group 45C, and the lower surface is Red Group 45B.

*Sepals.*—Size: Average 25 mm long×5 mm wide. Shape: Sepals generally acuminate. Sepal apex is generally cirrose. Weak foliaceous appendages on three of the five sepals. Base is flat at union with receptacle. Quantity: Five. Margins: Ciliated with fine hairs and stipitate glands. Surface texture: Inner side: Covered in fine hairs. Outer surface: Smooth, with limited number of stipitate glands present. Color: Upper surface Yellow-Green Group 146C. Lower surface Yellow-Green Group 144A.

Receptacle:

*Surface.*—Smooth.

*Color.*—Yellow-Green Group 144A.

*Shape.*—Pear-shaped.

*Size.*—7 mm (h)×5 mm (w).

Pedicels:

*Surface.*—Smooth, with moderate to abundant numbers of stipitate glands.

*Length.*—15-20 mm average length.

*Diameter.*—2 mm average diameter.

*Color.*—Yellow-Green Group 144A, with intonations of Greyed-Red Group 182B.

*Strength.*—Moderate.

*Borne.*—Multiply. 5-7 buds per flowering stem.

Peduncle:

*Surface.*—Smooth, with moderate numbers of stipitate glands.

*Length.*—10-12 cm average length.

*Diameter.*—2-3 mm average diameter.

*Color.*—Yellow-Green Group 144A, with intonations of Greyed-Red Group 182B.

*Strength.*—Moderately strong.

Flower bloom:

*Fragrance.*—Light.

*Duration.*—On the plant 10 days. Long lasting. As a cut flower, 5 to 7 days. Senesced petals drop away cleanly.

*Size.*—Small flowered garden rose. When open, the average flower diameter is 60 mm and the average flower height is 25 mm.

*Form.*—Shape of flower when viewed from the side: Upon opening, upper part: Cupped. Upon opening, lower part: Flat. Open flower, upper part: Flattened convex. Open flower, lower part: Flat.

Color:

*Upon opening, petals.*—Outermost petals: Outer Side: Red Group 45A. Inner Side: Red Group 45B. Innermost petals: Outer Side: Red Group 45B. Inner Side: Red Group 45B.

*Upon opening, basal petal spots.*—Basal petal spot, outermost petals: Outer Side: Yellow-White Group 158D. Inner Side: Yellow Group 1D. Basal petal spot, innermost petals: Outer Side: Yellow-White Group 158D. Inner Side: Yellow Group 1D.

*After opening, petals.*—Outermost petals: Outer Side: Red Group 53C. Inner Side: Red Group 46B. Innermost petals: Outer Side: Red Group 46B. Inner Side: Red Group 45A.

*After opening, basal petal spots.*—Basal petal spot, outermost petals: Outer Side: Yellow-White Group 158D. Inner Side: Yellow Group 1. Basal petal spot, innermost petals: Outer Side: Yellow-White Group 158D. Inner Side: Yellow Group 1D. Variegations: None.

General tonality: On open flower Red Group 45A. No change in the general tonality at the end of the $8^{th}$ day. Afterwards, general tonality is Red Group 45C.

Petals:

*Petal count.*—Approximately 10-12 petals under normal conditions.

*Petal reflex.*—Petals reflex slightly.

*Petal edge.*—Entire.

*Petal shape.*—Deltoid. Apex shape is round. Shape of base is acute.

*Petal size.*—35 mm long; 30 mm wide.

*Thickness.*—Thin.

*Petal arrangement.*—Generally in a regular pattern with overlapping edges.

Petaloids: Present.

*Petaloid count.*—Average of 4-7 per flower.

*Petaloid edge.*—Entire.

*Petaloid texture.*—Smooth.

*Petaloid shape.*—Linear to elliptic.

*Petaloid size.*—Petaloids are 20 mm long and 15 mm wide.

*Petaloid color.*—Color of inner side is Red Group 45A. Color of outer side is Red Group 45A.

Reproductive organs:

*Pistils.*—Approximately 20 present. Stigmas: Location: Superior in position to anthers. Color: Yellow Group 11B. Styles: Length: 9 mm long. Color: Yellow Group 11C.

*Stamens.*—Approximately 35-45 on average and regularly arranged. Anthers: Size: 2 mm long. Color: Gray-Orange Group 175C. Pollen: Generally present. Color: Yellow-Orange Group 20A. Filaments: Color: Yellow Group 13B. Length: 7 mm.

THE PLANT

*Plant growth.*—Moderate vigor. Erect habit. When grown as a budded nursery plant the average plant height is 60 cm and the average plant width is 65 cm.

*Stems.*—Stem color: Young wood: Yellow-Green Group 144A. Older wood: Yellow-Green Group 144A. Stem surface: Young wood: Smooth. Older wood: Smooth.

*Prickles.*—Present. Incidence: 5-7 per 10 cm of juvenile stem. 0-3 per 10 cm of mature stem. Size: Average length: 8 mm. Color: Immature prickles: Gray-Red Group 182B. Mature prickles: Gray-Brown Group 199C with intonations of Gray-Red Group 182B. Senescing to Gray-Brown Group 199C. Shape: Flat to flattened-concave. Anthocyanin: Color Gray-Red Group 182B.

*Leaves and leaflets.*—Normally 5 leaflets on normal leaves in middle of the stem. Venation pattern: Pyramidal net pattern. Leaf size: 100 mm (l)×85 mm (w). Quantity: Abundant. Texture: Upper side of leaflet: Semi glossy. Smooth. Under side of leaflet: Matte. Smooth. Color, mature foliage: Upper Leaf Surface: Green Group 137A. Lower Leaf Surface: Green Group 138B. Color, juvenile foliage: Upper Leaf Surface: Yellow-Green Group 146A. Lower Leaf Surface: Yellow-Green Group 146B. Anthocyanin intonation: Present. Location: Intonations present on juvenile leaf margins and developing leaves.

*Stipules.*—Size: 25 mm long. 9 mm between the tips of the stipule. Main body of stipule 3-4 mm in width. Shape: Longitudinally flanged. Stipule color: Upper side: Green Group 137A. Lower side: Yellow-Green Group 144A. Presence of stipitate glands: Present on margins. Margins: Ciliate along the upper margins.

*Petiole.*—Length: 20 mm. Diameter: 2 mm. Petiole color: Yellow Group 144A. Underneath: Smooth. Stipitate glands: Limited numbers of stipitate glands on margins.

*Petiole rachis.*—Length: 40 mm. Diameter: 2 mm. Color: Yellow-Green Group 144A. Margins: Entire, with occasional stipitate glands. Prickles: Lacking. Stipitate glands: Limited numbers of stipitate glands on margins.

*Leaflets.*—Size: Average size of the terminal leaflet is 45 mm (l)×35 mm (w). Shape: Broadly ovate. Base: Broadly ovate. Apex: Ovate. Margins: Compound serrated. Texture: Leathery.

Hips formation: Observed. Size: 8 mm (w)×8 mm (h). Color: Yellow-Green Group 144C.

Winter hardiness: To date, the variety has been grown successfully in Zone 5.

Disease resistance: Above average resistance to Powdery mildew (*Sphaerotheca pannosa*) and blackspot (*Diplocarpon rosae*) diseases under normal growing conditions.

I claim:

1. A new and distinct variety of rose plant, as described and illustrated herein.

* * * * *

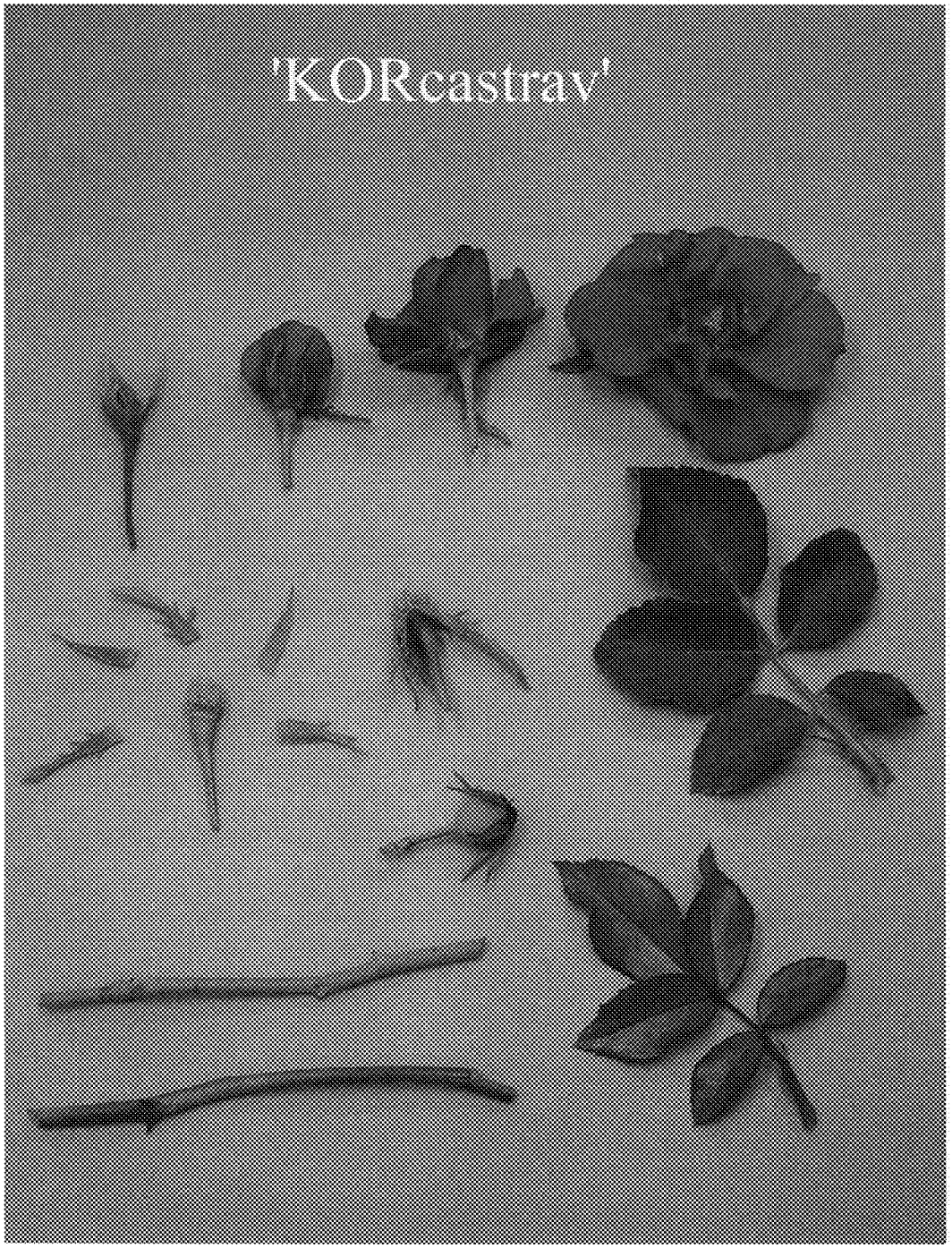
'KORcastray'